United States Patent [19]
Mehdizadeh

[11] Patent Number: 6,030,390
[45] Date of Patent: Feb. 29, 2000

[54] DISC SPACE SPREADER

[76] Inventor: Hamid M. Mehdizadeh, 14928 Diduca Way, Los Gatos, Calif. 95032

[21] Appl. No.: 09/329,096

[22] Filed: Jun. 9, 1999

Related U.S. Application Data

[63] Continuation-in-part of application No. 09/227,760, Jan. 8, 1999, abandoned.

[51] Int. Cl.[7] .................................................. A61B 17/16
[52] U.S. Cl. ............................................................ 606/84
[58] Field of Search ........................ 606/79, 84; 600/201, 600/235, 210, 213

[56] References Cited

U.S. PATENT DOCUMENTS

| | | | |
|---|---|---|---|
| 1,384,330 | 7/1921 | Moshier | 606/84 X |
| 4,239,045 | 12/1980 | Schlein | 606/84 X |
| 4,881,534 | 11/1989 | Uhl et al. | 606/79 X |
| 4,944,744 | 7/1990 | Ray | 606/79 |
| 5,803,904 | 9/1998 | Mehdizadeh | 600/235 |
| 5,961,522 | 10/1999 | Mehdizadeh | 606/79 |

FOREIGN PATENT DOCUMENTS

| | | | |
|---|---|---|---|
| 3131496 | 2/1983 | Germany | 606/79 |
| 1162415 | 6/1985 | U.S.S.R. | 606/79 |
| 1718852 | 3/1992 | U.S.S.R. | 606/79 |

OTHER PUBLICATIONS

"Ray Threaded Fusion Cage" and "Ray TFC™ Device System," PLIF Surgical Technique Manual, Surgical Dynamics, Inc., Norwalk, CT. (no date).

Primary Examiner—Jeffrey A. Smith
Attorney, Agent, or Firm—Henry M. Stanley

[57] ABSTRACT

An insertable and removable disc space spreader is provided for maintaining proper space between adjacent vertebral bodies during laminectomy procedures. In general, the disc space spreader of this invention provides a more gradual and therefore gentler entry into the intradiscal space and subsequently fewer traumas to bone and tissue contained therein than previously known spreaders. The spreader, in one embodiment, is able to form grooves in the vertebral bodies to subsequently facilitate insertion of a tang retractor used in these procedures.

12 Claims, 2 Drawing Sheets

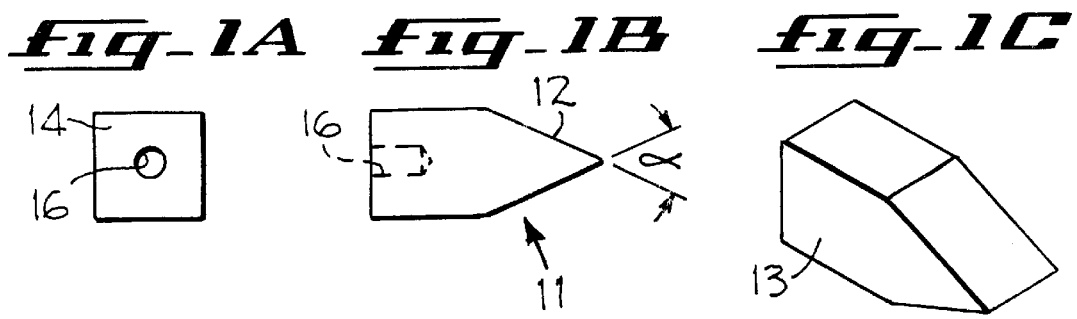

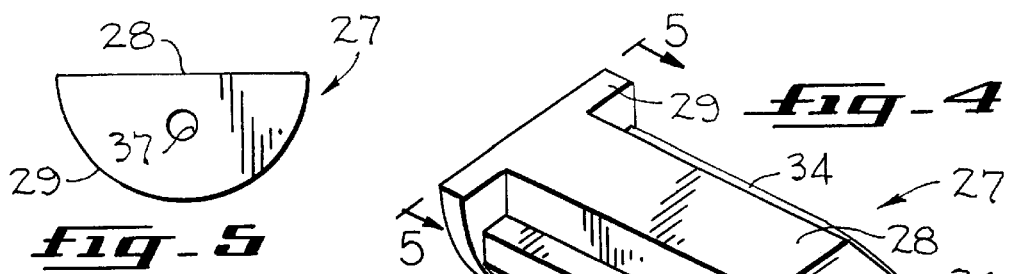
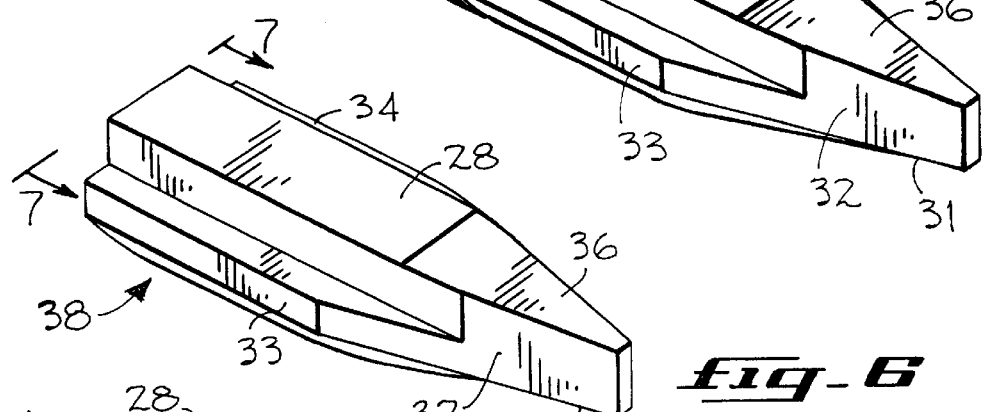
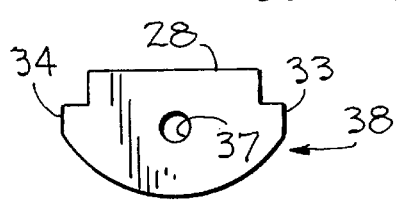
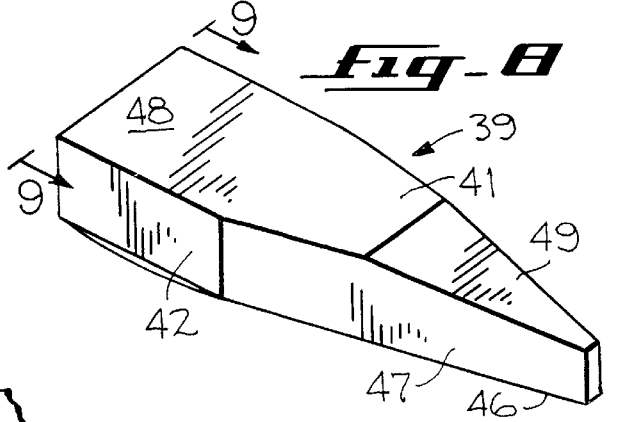
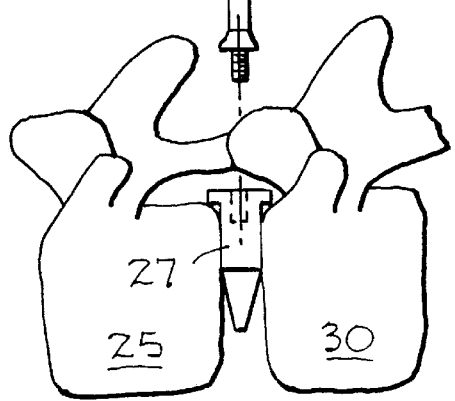
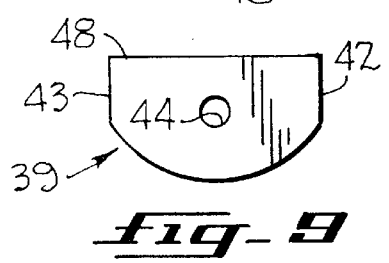

DISC SPACE SPREADER

This is a Continuation-in-Part patent application of U.S. patent application Ser. No. 09/227,760, filed Jan. 8, 1999 (now abandoned).

SUMMARY OF THE INVENTION

A disc space spreader is disclosed herein for use in laminectomy procedures in cooperation with an insertion and retraction tool. A main spreader body has a proximal end and a distal end with a wedge extending from the distal end of the main spreader body. The wedge has a wedge angle which is less than forty-five degrees. First and second elongate cutting splines are formed on opposing sides of the main spreader body are present together with a shoulder on the proximal end of the main spreader body. Further, means is provided for releasably engaging the insertion and retraction tool, such means being formed on the proximal end of the main spreader body.

A disc space spreader is disclosed for use in laminectomy procedures in cooperation with an insertion and retraction tool. A spreader body has a distal end and a proximal end and a wedge that extends from the spreader body distal end. The wedge has converging surfaces wherein the wedge has an inner side and an opposing outer side extending between the converging surfaces. The inner side has a convex cylindrical surface. First and second lateral cutting splines are provided on opposing sides of the spreader body. Further, means is provided on the proximal end of the spreader body for releasably engaging the insertion and retraction tool.

A disc space spreader is disclosed for use in laminectomy procedures in cooperation with an insertion and retraction tool. A spreader body has a distal end and a proximal end and a wedge that extends from the spreader body distal end. The wedge has converging surfaces forming a wedge angle that is less than forty-five degrees. The wedge further has an inner side and an opposing outer side. First and second lateral cutting splines are provided on opposing sides of the spreader body. Means is provided on the proximal end of the spreader body for releasably engaging the insertion and retraction tool. Further, a ramp is provided on the opposing outer side of the wedge.

A disc space spreader is provided for use in laminectomy procedures in cooperation with an insertion and retraction tool. A main spreader body has a proximal end and a distal end with a wedge extending from the distal end of the main spreader body. The wedge has an inner side and an opposing outer side. The inner side has a convex cylindrical shape. Means is provided on the proximal end of the main spreader body for releasably engaging the insertion and retraction tool.

A disc space spreader is provided for use in laminectomy procedures in cooperation with an insertion and retraction tool. A main spreader body has a proximal end and a distal end with a wedge extending from the distal end of the main spreader body. The wedge has converging surfaces forming a wedge angle, which is less than forty-five degrees. The wedge also has an inner side and an opposing outer side. Means is provided on the proximal end of the main spreader body for releasably engaging the insertion and retraction tool. A ramp is formed on the opposing outer side of the wedge.

A disc space spreader is described for use in laminectomy procedures in cooperation with an insertion and retraction tool. A main spreader body has a proximal end and a distal end. A wedge extends from the distal end having converging upper and lower surfaces terminating at an apex having an included angle less than forty-five degrees. The main spreader body has an inside surface and an outside surface extending from the proximal end to the apex. The inside surface has a convex cylindrical shape.

BRIEF DESCRIPTION OF THE DRAWINGS

FIGS. 1A through 1C depict a simplified embodiment of the present invention.

FIG. 2 shows an insertion and retraction tool for use in laminectomy procedures.

FIG. 3 is a perspective of a tang retractor for use in laminectomy procedures.

FIG. 4 is a perspective of one embodiment of the present invention.

FIG. 5 is a view along the line 5—5 of FIG. 4.

FIG. 6 is a perspective of another embodiment of the present invention.

FIG. 7 is a view along the line 7—7 of FIG. 6.

FIG. 8 is a perspective of yet another embodiment of the present invention.

FIG. 9 is a view along the line 9—9 of FIG. 8.

FIG. 10 is a view of the invention in place between vertebrae.

DESCRIPTION OF THE PREFERRED EMBODIMENTS

Disc space spreaders are used during laminectomy procedures to maintain a desired space between adjacent vertebrae on one side of the centerline of the spine while other laminectomy procedures are in process on the opposing side of the spine centerline. A basic embodiment of the invention disclosed herein takes the form of the disc space spreader shown in FIGS. 1A through 1C. An elevation of the disc space spreader 11 is shown in FIG. 1B with a wedge 12 extending from a distal end thereof. The wedge has a wedge angle indicated at alpha, which is less than forty-five degrees, in the neighborhood of 35–40 degrees as shown. A perspective of the spreader is seen in FIG. 1C having a flat side surface 13 and a similar opposing flat side surface (not shown). A proximal end 14 of the disc space spreader is seen in FIG. 1A having a centrally located threaded blind hole 16 therein. The disc space spreader 11, having an appropriate size, is inserted between vertebrae as hereinafter described, wherein the end position of the spreader is largely left to the discretion of the attending surgeon.

An insertion and retraction tool 17 is shown in FIG. 2 having a threaded extension 18 on one end thereof which is configured to engage the threads in the threaded blind hole 16. The insertion/retraction tool 17 has a slender shank 19 extending to an end thereof opposite the threaded extension on which is formed a knurled impact cap 21. The tool 17 is used to place the disc space spreader between adjacent vertebrae and is then disengaged and removed while laminectomy procedures progress. When it is necessary to remove the disc space spreader, the tool 17 is re-engaged in the threaded hole 16 and withdrawn with the disc space spreader attached.

FIG. 3 shows a tang retractor 22, which is disclosed and claimed in Applicant's U.S. Pat. No. 5,803,904 issued on Sep. 8, 1998. The tang retractor is tubular in shape, has a single tang 23 extending from the distal end thereof and an impact cap 24 on the proximal end. The tang 23 is joined to the distal end of the tang retractor 22 at shoulders 26 on each side thereof. The tang retractor is driven between adjacent vertebrae by tapping on the impact cap as described herein and in Applicant's U.S. Pat. No. 5,803,904 Patent.

Turning now to FIG. 4, a perspective of one embodiment 27 of the disc space spreader is shown. A main body portion 28 of the disc space spreader is shown having a shoulder 29 at a proximal end thereof and a wedge 31 extending from a distal end thereof. The wedge 31 has opposing surfaces thereon which converge at a free end of the wedge. One of the converging surfaces 32 is shown in FIG. 4. An elongate cutting spline 33 is also shown in FIG. 4 extending from the shoulder 29 on the proximal end of the disc space spreader 27 to the wedge 31 projecting from the distal end thereof. Just visible on the opposite side of the main spreader body 28 from the cutting spline 33 is another cutting spline 34 positioned in mirror image to the cutting spline 33. A ramp 36 is shown in FIG. 4 extending from the distal end of the main spreader body 28 to the free end of the wedge 31 and spanning the distance between the one converging side 32 and the opposing converging side (not shown) of the wedge 31. The ramp 36 extends from a position adjacent the upper surface of the main spreader body 28 downwardly toward the apex of the wedge 31. The converging sides of the wedge 31 include an angle, which is less than forty-five degrees and is typically in the range of twenty-five to thirty-five degrees. The main spreader body 28 has a lower surface portion 35 extending to the apex of the wedge 31 that is convex and cylindrical as seen in FIG. 5. As will be further explained hereinafter, the upper surface containing the ramp 36 is termed the outside surface and the lower surface is termed the inner surface.

During laminectomy procedures the tang retractor 22 (FIG. 3) is driven between a pair of adjacent vertebrae until the tang 23 is positioned fully between adjacent vertebrae and the shoulders 26 thereon are seated on the edges of each adjacent vertebral body. Previous to the insertion of the tang retractor the disc space spreader 27 (or 11, FIGS. 1A–1C) is engaged by the insertion/retraction tool 17 (FIG. 2) by engaging the threaded shank 18 in a threaded hole 37 seen in FIG. 5 which is similar to the threaded hole 16 in FIGS. 1A–1C, and the disc space spreader is driven into position between the adjacent vertebrae by tapping the knurled impact cap 21 with a mallet. The disc space spreader 27 is driven between the adjacent vertebrae until the shoulder 29 thereon seats against the edges of the adjacent vertebrae. The disc space spreader is shown in position in FIG. 10 wherein the disc space spreader is positioned toward the surface of the paper from a center line running through a series of vertebrae (two of which are shown at 25 and 30) of which the spine is constructed. On the opposite side of the center line (away from the surface of the paper in FIG. 10) a similar disc space spreader 27 may be inserted between the same two vertebrae as seen in FIG. 10 so that the vertebrae are spaced apart at positions on opposing sides of the center line. One of the disc space spreaders 27 is removed from its position between the vertebrae (FIG. 10) by inserting the threaded shank 18 into the threaded hole 37, engaging the disc space spreader and applying pressure outward to remove the disc space spreader from its position between the vertebrae. The disc space spreaders come in a variety of sizes to accommodate patient anatomical differences wherein the sizes correspond to the variety of sizes of tang retractors 22 as explained in the aforementioned U.S. Pat. No. 5,803,904. Upon withdrawal of the disc space spreader 27 a pair of grooves remain in the adjacent vertebrae which have been formed by the cutting splines 33 and 34 at opposing sides of the cylindrical surface portion 35. These grooves are formed by the disc space spreader 27 so as to accept the tang 23 in the corresponding size of the retractor tang 22 (FIG. 3). The tubular retractor and tang 23 have an outer surface similar to cylindrical surface portion 35. Thus, the tang 23 is readily inserted in proper position between the vertebrae to continue with the laminectomy procedure.

Another embodiment of the disc space spreader of the present invention is shown at 38 in FIG. 6. The disc space spreader 38 is similar to the disc space spreader 27 of FIG. 4 in all respects except that it does not have shoulder 29 on the proximal end thereof. All other portions of the disc space spreader 38 are assigned item numbers, which are the same as those assigned in FIG. 4, where structure and function are substantially the same. The cutting splines 33 and 34 in the embodiment of FIG. 6 perform the same function as those like items in the embodiment of FIG. 4. Thus, the tang retractor 22 may be easily entered into the disc space upon retraction of the disc space spreader, wherein the tang 23 on the tang retractor of FIG. 3 takes position in the grooves formed by the cutting splines as hereinbefore described. The proximal end of the disc space spreader 38 also has the threaded blind hole 37 formed therein for releasably accepting the threaded shank 18 on the insertion/retraction tool 17 shown in FIG. 2. Moreover, the angle of the wedge extending from the distal end of the main spreader body 28 is less than forty-five degrees, preferably within the range of twenty-five to thirty-five degrees. As is the case with the disc space spreader 27 of FIG. 4, the disc space spreader 38 has the ramp 36 formed on the wedge 31 extending from the distal end of the main spreader body 28 so that a minimum of bone and tissue will be contacted by the disc space spreader (other than by the cutting splines 33 and 34). This function assumes importance because the shallower angle of the wedge 31 allows the disc space spreader of the embodiments disclosed herein to enter further into the intradiscal space than previously known disc space spreaders. For purposes of description and because when the disc space spreader is positioned between vertebrae, the ramp 36 is facing outwardly toward outside of the vertebrae, the ramp 36 is said to be on the outer side of the spreaders 27 and 38.

In another relatively simple form, the disc space spreader of the present invention is shown at 39 in FIG. 8 of the drawings wherein a main spreader body 41 has opposing sides 42 and 43 (FIG. 9). A threaded blind hole 44 is formed in a proximal end of the main spreader body 41 so that the disc space spreader 39 may be engaged with and disengaged from the insertion/retraction tool 17 of FIG. 2. A wedge 46 extends from the distal end of the main spreader body 41 as seen in FIG. 8. The wedge 46 has converging surfaces on the opposing sides thereof, one of which converging surfaces 47 is shown in FIG. 8. The converging surface 47 and the opposing surface (not shown) of wedge 46 meet at an apex or free end and include an angle which is less than forty-five degrees, is preferably in the range of twenty-five to thirty-five degrees. Main spreader body 41 has an upper surface 48 thereon. A ramp 49 intersects the upper surface 48 at a position toward the main spreader body and extends downward distally terminating at the apex of the wedge 46. The ramp 49 provides for a smaller tip at the apex of the wedge 46 so that bone and tissue in the intravertebral space is avoided. This is a beneficial feature because the wedge 46 includes a smaller angle than used heretofore and therefore extends to further into the intravertebral space. The ramp 49, as with the ramps 36 of FIGS. 4 and 6, is referred to as positionally on the "outside" of the disc space spreader 39. The cylindrical portion 35, corresponding to the surface assigned that item number in the previous embodiments, is referred to as positionally on the "inside" of the disc space spreader 39.

FIG. 10, as mentioned hereinbefore, shows the releasable engagement of any of the embodiments 11, 27, 38 and 39 of the disc space spreader of the present invention by the insertion/retraction tool 17. To insert or remove the disc space spreader, the threaded shank 18 on the insertion retraction tool 17 is engaged with the internal threads in the threaded blind holes 16, 37 or 44. The tool 17 is then either tapped inwardly to insert the disc space spreader into or forced outwardly to pull the disc space spreader out of the intradiscal space between adjacent vertebrae 25 and 30. It is envisioned that the embodiments of FIGS. 1A–1C, 6 and 8 of the disc space spreader disclosed herein are usable without the shoulder 29 thereon through the use of visual or fluoroscopic control. Further it is envisioned that the disc space spreaders of the present invention are usable with the single tang retractor 22 of FIG. 3 as well as with the double tang retractor discussed and compared in the aforementioned U.S. Pat. No. 5,803,904. While the disc space spreaders of this invention are in a variety of sizes to correspond with the variety of sizes of tang retractors and associated surgical tools to accommodate various anatomical sizes in patients, a typical disc space spreader might be 21 mm or so in length and 9 mm or so across the outer surfaces of the cutting splines described herein. Precise sizes will depend upon the graduations in the various sets of instruments for performing laminectomies and will be selected dependent upon the anatomical characteristics of the patient.

Although the best mode contemplated for carrying out the present invention has been shown and described herein, it will be understood that modification and variation may be made without departing from what is regarded to be the subject matter of the invention.

What is claimed:

1. A disc space spreader for use in laminectomy procedures in cooperation with an insertion and retraction tool, comprising
    a main spreader body having a proximal end and a distal end,
    a wedge extending from said distal end of said main spreader body, said wedge having a wedge angle less than forty five degrees,
    first and second elongate cutting splines on opposing sides of said main spreader body,
    a shoulder on said proximal end of said main spreader body, and
    means for releasably engaging the insertion and retraction tool on said proximal end.

2. The disc space spreader of claim 1, comprising a ramp on said wedge.

3. The disc space spreader of claim 1, wherein said main spreader body has an inner side and an opposing outer side, comprising
    a convex cylindrical surface on said inner side.

4. A disc space spreader for use in laminectomy procedures in cooperation with an insertion and retraction tool, comprising
    a spreader body having a distal end and a proximal end,
    a wedge extending from said spreader body distal end, said wedge having converging surfaces, said wedge also having an inner side and an outer side extending between said converging surfaces, said inner side having a convex cylindrical shape,
    first and second lateral cutting splines on opposing sides of said spreader body, and
    means for releasably engaging the insertion and retraction tool on said proximal end.

5. A disc space spreader for use in laminectomy procedures in cooperation with an insertion and retraction tool, comprising
    a spreader body having a distal end and a proximal end,
    a wedge extending from said spreader body distal end, said wedge having converging surfaces, forming a wedge angle less than forty five degrees,
    first and second lateral cutting splines on opposing sides of said spreader body, and
    means for releasably engaging the insertion and retraction tool on said proximal end, wherein said wedge has an inner side and an opposing outer side extending between said converging surfaces, further comprising a ramp on said opposing outer side.

6. The disc space spreader of claim 5, comprising a shoulder on said proximal end.

7. A disc space spreader for use in laminectomy procedures in cooperation with an insertion and retraction tool, comprising
    a main spreader body having a proximal end and a distal end,
    a wedge extending from said distal end of said main spreader body, said wedge having an inner side and an opposing outer side, said inner side having a convex cylindrical shape, and
    means for releasably engaging said insertion and retraction tool on said proximal end.

8. The disc space spreader of claim 7, comprising first and second elongate cutting splines on opposing sides of said main spreader body.

9. A disc space spreader for use in laminectomy procedures in cooperation with an insertion and retraction tool, comprising
    a main spreader body having a proximal end and a distal end,
    a wedge extending from said distal end of said main spreader body, said wedge having converging surfaces forming a wedge angle less than forty five degrees, and
    means for releasably engaging said insertion and retraction tool on said proximal end,
wherein said wedge has an inner side and an opposing outer side extending between said converging surfaces, further comprising
    a ramp on said opposing outer side.

10. The disc space spreader of claim 9, comprising a shoulder on said proximal end.

11. A disc space spreader for use in laminectomy procedures in cooperation with an insertion and retraction tool, comprising
    a main spreader body having a proximal end and a distal end,
    a wedge extending from said distal end, said wedge having converging upper and lower surfaces terminating at an apex and having an included angle less than forty-five degrees,
    said main spreader body having inside and outside surfaces extending from said proximal end to said apex,
    said inside surface having a convex cylindrical shape.

12. The disc space spreader of claim 11 wherein said main spreader body outside surface comprises
    a ramp on said wedge extending to said apex.

* * * * *